United States Patent [19]
Vetter et al.

[11] Patent Number: 5,785,691
[45] Date of Patent: Jul. 28, 1998

[54] SYRINGE CAP ASSEMBLY

[75] Inventors: Helmut Vetter, Ravensburg; Thomas Otto, Weingarten, both of Germany

[73] Assignee: Arzneimittel GmbH Apotheker Vetter & Co. Raversburg, Ravensburg, Germany

[21] Appl. No.: 724,075

[22] Filed: Sep. 30, 1996

[30] Foreign Application Priority Data

Oct. 6, 1995 [DE] Germany .................. 195 37 163.1

[51] Int. Cl.⁶ ............................................ A61M 5/50
[52] U.S. Cl. .................. 604/187; 604/905; 215/DIG. 3
[58] Field of Search ........................ 604/181, 187, 604/199, 200, 263, 905; 215/250, DIG. 3

[56] References Cited

U.S. PATENT DOCUMENTS

| 4,240,425 | 12/1980 | Akhavi. |
| 4,667,837 | 5/1987 | Vitello. |
| 5,624,405 | 4/1997 | Futagawa et al.. |

FOREIGN PATENT DOCUMENTS 0 397 951  11/1990  European Pat. Off..

*Primary Examiner*—Michael Buiz
*Assistant Examiner*—David O. Reip
*Attorney, Agent, or Firm*—Herbert Dubno; Andrew Wilford

[57] ABSTRACT

A syringe assembly has a syringe body adapted to be filled with an injectable liquid and having an annular neck defining an axis forming an axially outwardly open outlet and a needle insert fitting in and blocking the outlet and formed with an axially throughgoing passage so that a needle can be inserted axially through the passage of the insert into the body. A retaining collar engaged around the neck holds the insert in the outlet and a plug engaged in the passage fits over the retaining collar. A retaining ring fixed around the collar at the neck holds the collar on the neck and has an annular and axially outwardly directed end edge. A cup-shaped safety cap bearing axially inward on the plug has an annular and axially inwardly directed end edge confronting the retaining-ring edge and spaced axially therefrom by a gap which is bridged by a plurality of angularly spaced frangible webs unitarily formed with the ring and with the cap and extending from the cap edge to the ring edge. A plurality of angularly spaced spacer blocks formed on one of the edges and alternating with the webs project at least partially across the gap toward the other edge.

12 Claims, 2 Drawing Sheets

SYRINGE CAP ASSEMBLY

FIELD OF THE INVENTION

The present invention relates to a medical syringe. More particularly this invention concerns a cap assembly for a normally prefilled, ready-to-use syringe.

BACKGROUND OF THE INVENTION

A standard syringe has a syringe body adapted to be filled with an injectable liquid and having an annular neck defining an axis forming an axially outwardly open outlet and a needle insert fitting in and blocking the outlet and formed with an axially throughgoing passage. Thus a needle can be inserted axially through the passage of the insert into the body. A retaining collar engaged around the neck holds the insert in the outlet and a plug or tip cap engaged in the passage fits over the retaining collar. A retaining ring fixed around the collar at the neck holds the collar on the neck and has an annular and axially outwardly directed end edge. A cup-shaped safety cap bears axially inward on the plug and has an annular and axially inwardly directed end edge confronting the retaining-ring edge and spaced axially therefrom by a gap. A plurality of angularly spaced frangible webs unitarily formed with the ring and with the cap extend from the cap edge to the ring edge.

Thus with this system as described in EP 0,397,951 the cap can be twisted off, breaking the webs, to expose the plug and allow it to be removed so that a needle assembly can be fitted to the collar and insert. This type of arrangement is particularly useful for prefilled syringes that only need to have a needle mounted on them to make them ready for use.

The problem with such an arrangement is that the subassembly of the cap and retaining ring joined by the webs is fairly fragile, especially before it is installed. As it is pressed axially down over the collar substantial compressive force is exerted on the webs which can fracture, rendering the cap useless. Furthermore during handling and transport after assembly it is possible for the cap to be subjected to considerable axially inwardly directed forces that can crush and destroy the webs, again ruining the syringe assembly.

OBJECTS OF THE INVENTION

It is therefore an object of the present invention to provide an improved syringe assembly.

Another object is the provision of such an improved syringe assembly which overcomes the above-given disadvantages, that is which is substantially more durable than the prior-art arrangements.

SUMMARY OF THE INVENTION

A syringe assembly has according to the invention a syringe body adapted to be filled with an injectable liquid and having an annular neck defining an axis forming an axially outwardly open outlet and a needle insert fitting in and blocking the outlet and formed with an axially throughgoing passage so that a needle can be inserted axially through the passage of the insert into the body. A retaining collar engaged around the neck holds the insert in the outlet and a plug engaged in the passage fits over the retaining collar. A retaining ring fixed around the collar at the neck holds the collar on the neck and has an annular and axially outwardly directed end edge. A cup-shaped safety cap bearing axially inward on the plug has an annular and axially inwardly directed end edge confronting the retaining-ring edge and spaced axially therefrom by a gap which is bridged by a plurality of angularly spaced frangible webs unitarily formed with the ring and with the cap and extending from the cap edge to the ring edge. According to the invention a plurality of angularly spaced spacer blocks formed on one of the edges and alternating with the webs project at least partially across the gap toward the other edge. These blocks are not connected to this other edge but instead either bear axially against it or are slightly axially spaced from it.

Thus with this arrangement the spacer blocks form the force-transmitting connection between the cap and the ring during assembly and subsequent handling of the assembly. The webs are slightly axially compressible so that when the cap/ring subassembly is pushed axially onto the retaining collar, the blocks bear on the ring and transmit the axial force without substantial stress to the webs. Nonetheless since the blocks are not connected at both ends, they do not make it harder to break off the cap when that is necessary.

According to the invention the webs each extend along a helix centered on the axis and are angularly equispaced about the axis. Thus they have some axial elasticity. These webs taper axially and are pyramidal. On the other hand the spacer blocks are generally trapezoidal and taper from the one edge to the other edge.

The retaining ring in accordance with the invention has a formation locking it to the collar which can be a radially inwardly directed lip engaged behind the collar. This makes it easy to put together the assembly simply by pushing the cap/ring subassembly down over the insert. Furthermore the cap is formed on the axis with a throughgoing hole smaller in diameter than the plug and the safety cap has an end wall bearing axially inward on the plug. The cap tapers axially outwardly and the blocks are unitarily formed with the cap edge.

BRIEF DESCRIPTION OF THE DRAWING

The above and other objects, features, and advantages will become more readily apparent from the following description, reference being made to the accompanying drawing in which.

SPECIFIC DESCRIPTION

Figure 1:
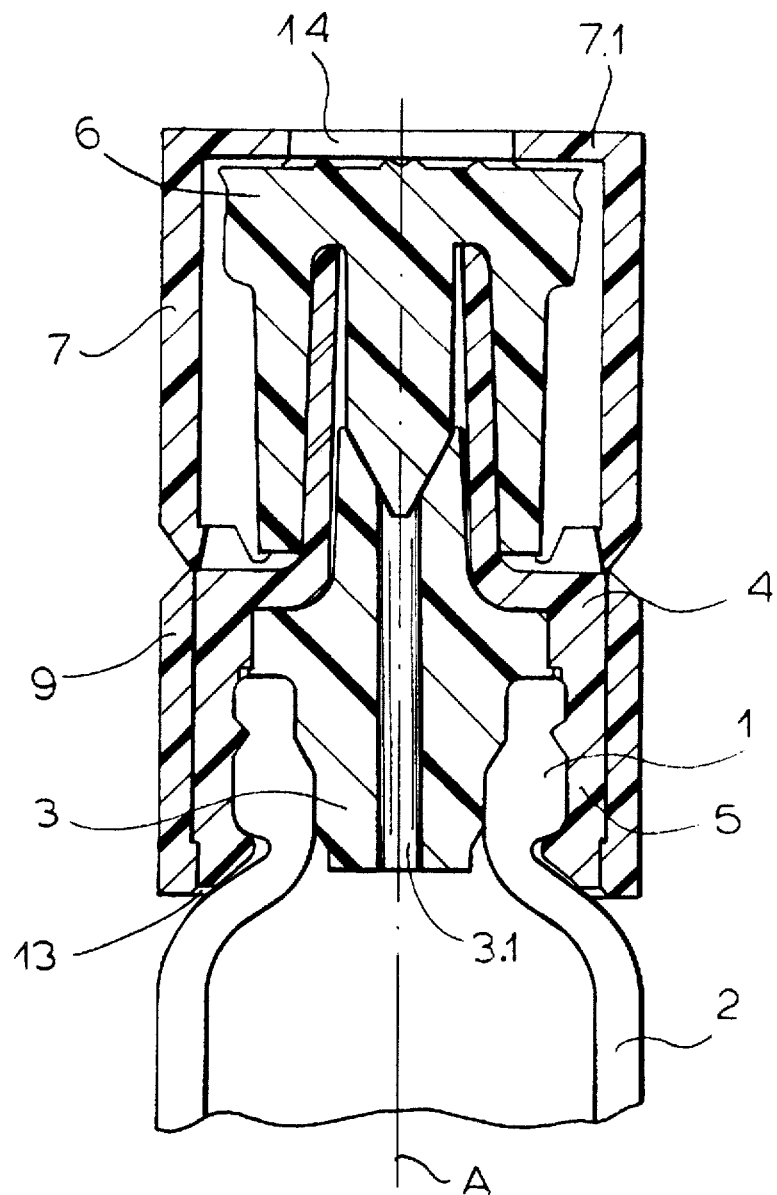
FIG. 1 is an axial section through the end of a syringe according to the invention.

As seen in FIG. 1 a standard glass or plastic syringe body 2 centered on an axis A has a neck 1 defining an outlet that is plugged by an elastomeric insert 3 formed with an axially throughgoing passage 3.1. A retaining collar 4 fits over the needle insert 3 and engages with radially outwardly deflectable legs 5 around the neck 1 to hold this insert 3 in place while providing a seat for a needle that is inserted through the passage 3.1. The body 2 is adapted to be filled with an injectable liquid and may be subdivided into two compartments and provided with a bypass as is known in the art. In addition of course a piston is provided in the body and its rear end has gripping formations.

A plug or tip cap 6 is engaged in the insert 3 and into the conically outwardly flared end of the passage 3.1 to block it. This plug 6 maintains the contents of the body 2 against leakage. A safety cap 7 which can be tapered radially outward (up in the drawing) has an end wall 7.1 bearing axially inward on the plug 6 and is attached by webs 10 to a retaining ring 9 that fits around the fingers 5 of the collar 4. The ring 9 therefore locks the collar 4 on the neck 1 over the insert 3 and the cap 7 holds the plug 6 in place, bearing axially inward on the insert 3. The end wall 7.1 is formed centered on the axis with a hole 14 of slightly smaller diameter than the plug 6 so that the user can ascertain that the plug 6 is properly in place without opening the package.

Figure 3:
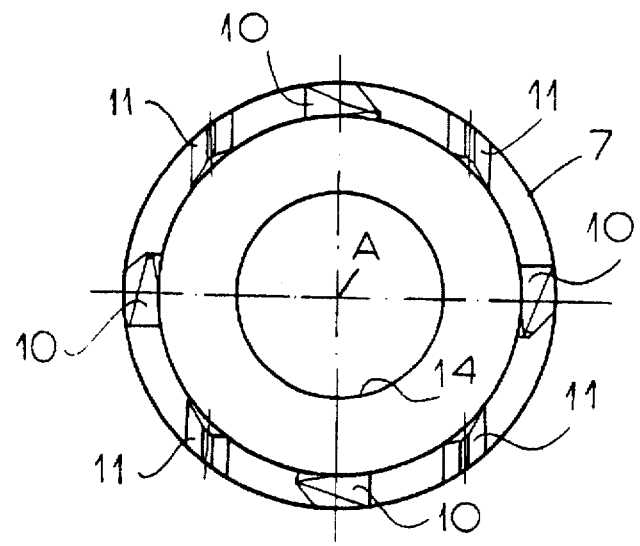
FIG. 3 is a section taken along line III—III of FIG. 2.
Figure 2:
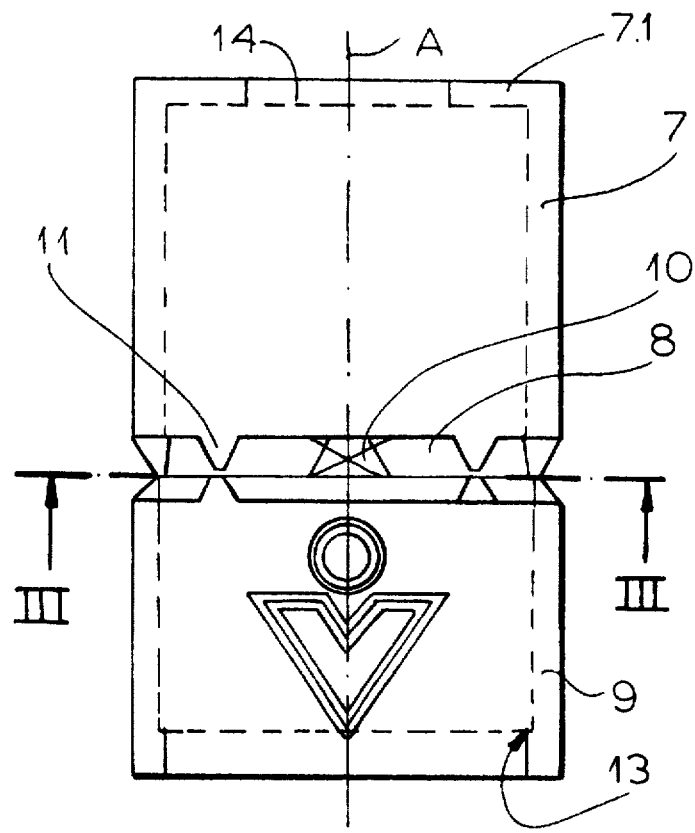
FIG. 2 is a side view of the cap and retaining ring of the syringe of FIG. 1.

The webs 10 as shown in FIG. 3 are angularly equispaced about the axis A and extend along respective helices centered on the axis A, so that they have some angular and radial strength but are axially compressible. These webs 10 are of pyramidal shape and frangible so that the cap 7 can be twisted off to allow the user to pull out the plug 6 and fit a needle assembly to the collar 4.

According to the invention the edge of the cap 7 turned toward the edge of the ring 9 is formed with a plurality of spacer blocks 11 alternating with the webs 10. These block 11 are of trapezoidal shape and taper axially toward the ring 9. They bridge the gap formed between the axially spaced edges of the cap 7 and ring 9 and have outer ends that touch or are axially very closely juxtaposed with the edge of the ring 9.

Thus the assembly formed by the cap 7 and ring 9 is fitted over the collar 4 and plug 6 by simply axially pushing it down or inward until a lip 13 on the ring 9 snaps under an edge of the legs 5 of the collar 4, in which position the end wall 7.1 bears on the plug 6 to hold it in position. During such installation the blocks 11 bear axially on the ring 9 so that no significant force is transmitted through the frangible webs 10.

For use the cap 7 is pulled and twisted to tear the webs 10, allowing it to be lifted off the assembly. The plug 6 is then lifted off to expose the sterile end of the collar 4, and a needle assembly is fitted to this collar 4.

We claim:

1. A syringe assembly comprising:

a syringe body adapted to be filled with an injectable liquid and having an annular neck defining an axis forming an axially outwardly open outlet;

a needle insert fitting in and blocking the outlet and formed with an axially throughgoing passage, whereby a needle can be inserted axially through the passage of the insert into the body;

a retaining collar engaged around the neck and holding the insert in the outlet;

a plug engaged in the passage and fitting over the retaining collar;

a retaining ring fixed around the collar at the neck, holding the collar on the neck, and having an annular and axially outwardly directed end edge;

a cup-shaped safety cap bearing axially inward on the plug and having an annular and axially inwardly directed end edge confronting the retaining-ring edge and spaced axially therefrom by a gap;

a plurality of angularly spaced frangible webs unitarily formed with the ring and with the cap and extending from the cap edge to the ring edge; and a plurality of angularly spaced spacer blocks formed on one of the edges, alternating with the webs, and projecting at least partially across the gap toward the other edge.

2. The syringe assembly defined in claim 1 wherein the webs each extend along a helix centered on the axis.

3. The syringe assembly defined in claim 1 wherein the webs are angularly equispaced about the axis.

4. The syringe assembly defined in claim 1 wherein the webs taper axially.

5. The syringe assembly defined in claim 4 wherein the webs are pyramidal.

6. The syringe assembly defined in claim 1 wherein the spacer blocks are generally trapezoidal and taper from the one edge to the other edge.

7. The syringe assembly defined in claim 1 wherein the retaining ring has a formation locking it to the collar.

8. The syringe assembly defined in claim 7 wherein the formation is a radially inwardly directed lip engaged behind the collar.

9. The syringe assembly defined in claim 1 wherein the cap is formed on the axis with a throughgoing hole smaller in diameter than the plug.

10. The syringe assembly defined in claim 1 wherein the safety cap has an end wall bearing axially inward on the plug.

11. The syringe assembly defined in claim 1 wherein the cap tapers axially outwardly.

12. The syringe assembly defined in claim 1 wherein the blocks are unitarily formed with the cap edge.

* * * * *